(12) United States Patent
Church

(10) Patent No.: US 12,303,603 B2
(45) Date of Patent: May 20, 2025

(54) REAL-TIME COMPOUNDING 3D PRINTER

(71) Applicant: Sciperio, Inc, Orlando, FL (US)

(72) Inventor: Kenneth H. Church, Orlando, FL (US)

(73) Assignee: SCIPERIO, INC, Orlando, FL (US)

( * ) Notice: Subject to any disclaimer, the term of this patent is extended or adjusted under 35 U.S.C. 154(b) by 1250 days.

(21) Appl. No.: 15/628,215

(22) Filed: Jun. 20, 2017

(65) Prior Publication Data

US 2017/0360714 A1    Dec. 21, 2017

Related U.S. Application Data

(60) Provisional application No. 62/352,389, filed on Jun. 20, 2016.

(51) Int. Cl.

| | |
|---|---|
| *A61K 9/20* | (2006.01) |
| *A61J 3/00* | (2006.01) |
| *A61J 3/06* | (2006.01) |
| *B29C 64/314* | (2017.01) |
| *B33Y 40/10* | (2020.01) |
| *B33Y 50/00* | (2015.01) |
| *B33Y 50/02* | (2015.01) |
| *G06F 30/00* | (2020.01) |
| *G06F 119/18* | (2020.01) |
| *G06T 19/00* | (2011.01) |
| *G16H 20/10* | (2018.01) |
| *G16H 20/60* | (2018.01) |

(52) U.S. Cl.
CPC ............... *A61K 9/2072* (2013.01); *A61J 3/00* (2013.01); *A61J 3/06* (2013.01); *B33Y 40/10* (2020.01); *B33Y 50/02* (2014.12); *G06F 30/00* (2020.01); *G16H 20/10* (2018.01); *G16H 20/60* (2018.01); *B29C 64/314* (2017.08); *B33Y 50/00* (2014.12); *G06F 2119/18* (2020.01); *G06T 19/00* (2013.01)

(58) Field of Classification Search
CPC ...... A61K 9/20; A61J 3/00; A61J 3/06; B33Y 50/02; B33Y 40/10; B33Y 50/10; G16H 20/60; G16H 20/10; G06F 30/00; G06T 19/00; G06T 119/18; B29C 64/314
See application file for complete search history.

(56) References Cited

U.S. PATENT DOCUMENTS

| | | | |
|---|---|---|---|
| 10,653,622 B1 * | 5/2020 | Cetinkaya | A61K 9/2893 |
| 2004/0005360 A1 * | 1/2004 | Wang | A61K 9/2027 424/473 |
| 2016/0342769 A1 * | 11/2016 | DeCiccio | G06F 19/3456 |
| 2017/0156386 A1 * | 6/2017 | Baetge | A23K 20/00 |
| 2017/0335271 A1 * | 11/2017 | Maggiore | B29C 64/106 |

\* cited by examiner

*Primary Examiner* — Shirley V Gembeh
(74) *Attorney, Agent, or Firm* — Goodhue, Coleman & Owens, P.C.

(57) ABSTRACT

A method for delivery of personalized medication or nutrition for an individual is provided. The method includes receiving parameters for the personalized medication at a 3D printer, wherein the parameters comprise one or more ingredients, mixing at least one of the ingredients at the 3D printer, and micro-dispensing the one or more of the ingredients into dose form at the 3D printer.

20 Claims, 2 Drawing Sheets

REAL-TIME COMPOUNDING 3D PRINTER

RELATED APPLICATIONS

This application claims priority to U.S. Provisional Patent Application No. 62/352,389, filed Jun. 20, 2016, and entitled "Real-time Compounding 3D Printer", hereby incorporated by reference in its entirety.

FIELD OF THE INVENTION

The present invention relates to health care. More particularly, but not exclusively, the present invention relates to real-time compounding using a 3D printer.

BACKGROUND

Personalized medicine allows medications to be individually and specifically prepared for a particular patient. In contrast to mass produced medications, personalized medicines allows for customization in terms of strength, dosage forms, taste or flavor, allows for exclusions of particular ingredients due to sensitivities or allergies, and other patient specific properties.

Personalized medicine will require compounding. Compounding is mixing medications with specific and accurate volumes for specific individuals. Compounding is done with some automation, but a lot of hands on by pharmacists. This increases the time for compounding and increases the cost. The final form of the drug must be placed in a capsule or a liquid container for consumption. A need for rapid compounding exists.

SUMMARY

Therefore, it is a primary object, feature, or advantage of the present invention to improve over the state of the art.

It is a further object, feature, or advantage of the present invention to provide for rapid compounding to enable personalized medicine.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by an objects, features, or advantages stated herein.

According to one aspect, a method for delivery of personalized medication or nutrition for an individual is provided. The method includes receiving parameters for the personalized medication at a 3D printer, wherein the parameters comprise one or more ingredients, mixing at least one of the ingredients at the 3D printer, and micro-dispensing the one or more of the ingredients into dose form at the 3D printer.

According to another aspect, a system for delivery of personalized medication or nutrition for an individual is provided. The system includes a 3D printing platform comprising at least one micro-dispenser, a mixer for mixing at least one ingredient, and a control system operatively connected to the 3D printing platform and the mixer. The system is configured to receive parameters for the personalized medication at the control system, the parameters including at least one ingredient in powder or liquid form, mix the at least one ingredient using the mixer and micro-dispense the at least one ingredient into dose form using the at least one micro-dispenser.

According to another aspect, a method for delivery of personalized medication or nutrition for an individual according to a treatment program is provided. The method includes receiving parameters for the personalized medication at a 3D printer for a plurality of doses, wherein the parameters for each of the plurality of the doses comprise one or more ingredients and volumetric information for the one or more ingredients. The method further includes mixing at least one of the ingredients at the 3D printer, and micro-dispensing the one or more of the ingredients into dose form at the 3D printer to form the plurality of doses for the treatment program. The volumetric information for the one or more ingredients is different for different ones of the doses within the treatment program. In addition, each of the plurality of doses may include identifying information which may be conveyed through color coding, size and shape, characters or symbols or otherwise.

BRIEF DESCRIPTION OF THE DRAWINGS

Illustrated embodiments of the disclosure are described in detail below with reference to the attached drawing figures, which are incorporated by reference herein.

DETAILED DESCRIPTION

A real time compounding 3D printer allows for mixing in real time liquid or powder medications and then printing the capsule. In one aspect, the ingredients may be mixed into a biopolymer that can be consumed and then allow for time release of drugs are then possible. This may be performed by inputting the drug mixture and allowing the system to precisely control all volumes and mix and dispense or print in 3D in real time.

The system may have multi-material capability. Thus, multiple materials may be used which may include any number of materials suitable for either the medication or capsules or biopolymer. Biopolymers are any polymers that are biocompatible such as polycaprolactone or materials made to be biocompatible. Suitable materials include any drug in liquid or powder form. Materials may further include flavoring agents or other ingredients. The materials themselves may have a wide range of material viscosities including viscosities in the range of 1 centipoise to more than 1 million centipoise.

A mixer as a part of the 3D printer system may provide for mixing diverse types of materials in real-time. The material may be micro-dispensed into existing capsules or micro-dispensed into 3D capsules that are printed on the 3D printer system. Additional mixing may include mixing low and high viscous materials to include mixing while heating or cool. Where drugs are mixed into the biopolymer they can then be printed in any 3D shape and size thus eliminating the need to print in capsules.

It should be understood that each 3D printed pill or custom pill may be designed and constructed according to parameters such as strengths, dosage forms, flavors, or other parameters. For particular individuals, ingredients may be excluded due to allergies or other adverse reactions. Particular ingredients may be included based on particular preferences of a user such as flavor.

It should be understood that in addition to medications the methods and systems described herein may be used for formulating nutraceuticals, nutritional supplements, or other health supplements which do not necessarily require prescriptions from a health care provider.

Figure 1:
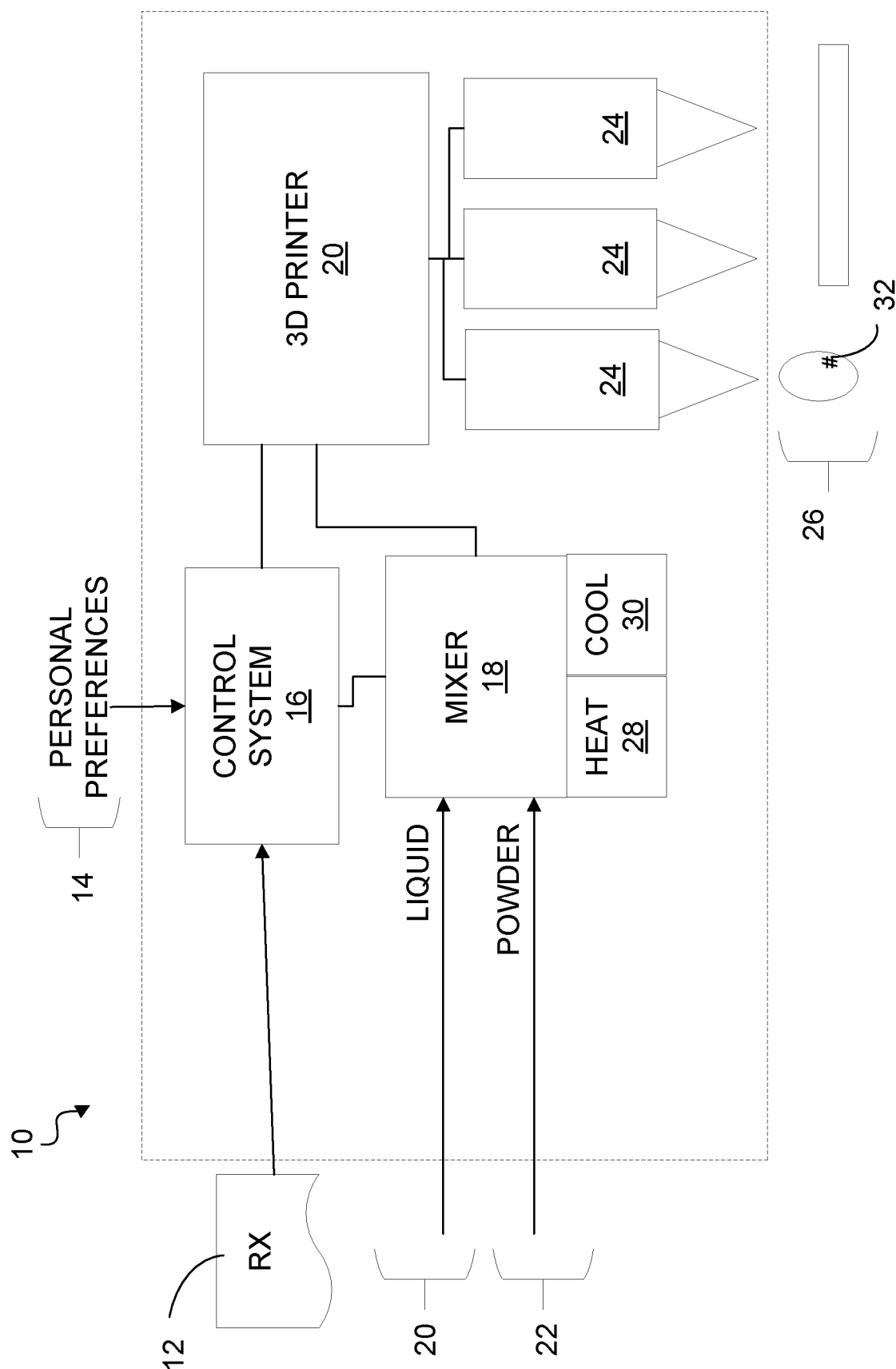
FIG. 1 illustrates one example of a block diagram of a system for personalized medication.

FIG. 1 illustrates one example of a system 10 for 3D printing. As shown in FIG. 10 a prescription 12 may be received as a set of input parameters at a control system 16. It is contemplated that the prescription 12 may be an electronic prescription from a health care provider. Either a single prescription or multiple prescriptions may be present. Prescription information may be for a particular amount of medication or active ingredient and the frequency that the medication can be taken or other instructions or directions for use. Information may include a recipe which may include a basis or chief ingredient, an adjuvant to assist its action, a corrective to prevent or lessen any undesirable effect, and a vehicle or excipient to make it suitable for administration and pleasant to the patient. Alternatively, this information may be otherwise input into the control system 16. In addition, the control system 16 may receive as input personal preferences 14 which may include preferences regarding flavoring agents or coloring agents or dosage forms. In addition, input may be received as personal preferences 14 or otherwise if the individual is allergic to certain types of potential ingredients or otherwise has adverse reactions to certain types of ingredients.

It is to be understood that because individual dosages of the medication are being created, there is a heretofore unknown level of customization that may be performed for each particular dose or across a plurality of different doses.

For example, the medication may be printed in a manner which promotes proper time release of the medication within the dose. This may be accomplished by layering the active ingredients at appropriate layers within the dosage form so that the medication is released over the time. Selection of other materials to include within the dose may be made to delay or increase the time of absorption to meet desired time release guidelines.

In another example, where a prescription (as opposed to an individual dose) is to last for a particular time period, the amount of an active ingredient may be decreased over the time period (e.g. the first dose may be significantly stronger than the last does). For example, for narcotic pain medications, the amount of active ingredient may be decreased over the length of the prescription in order to assist in avoiding dependency on the pain medications. Thus, customization may occur across a set of pills associated with a prescription.

Similarly, where an individual is taking multiple medications, multiple medications may be included in the same dose. Alternatively, where an individual must still take multiple medications, coloring agents may be added to help the individual distinguish between different doses. Alternatively, coloring agents may be used to assist an individual in determining when to take particular doses (e.g. blue bills at breakfast, yellow pills at lunch, green pills on Mondays, etc.). Thus, color coding may be used according to user preferences or across a set of medications taken by an individual to increase convenience to the user and increase compliance by the user.

In addition to color coding, it is contemplated that other forms of customization may be performed. The customization may included various types of identifying information. The identifying information may include color coding and/or may include characters or symbols or patterns including patterns encoding information such as two dimensional bar codes. In addition, different sizes or shapes may be used to identify a particular type of medication or supplement, the volumetric concentration of a particular ingredient, the schedule for taking the dose, or other information. The identifying information may also include information identifying the patient, or other information from a prescription, information identifying the 3D printer, or other information.

Once properly parameterized based on various inputs including from one or more prescriptions 12, personal preferences 14, additional parameters set by pharmacists or system parameters. For example, the system may provide for accessing databases of drug interactions and not allow certain drugs to be combined which would have the potential for adverse reactions.

A mixer 18 is shown. One or more mixers may be present as the system 10 may support multiple types of materials. The mixer 18 may receive liquid 20 and/or powder 22. The mixer 18 may be used for mixing diverse types of materials in real-time. Materials from the mixer 18 may be conveyed through the 3D printer 20 to one or more micro-dispensers 24. It is to be understood that the mixer 18 may be integrated into the 3D printer 20 in various ways and at various locations as may be appropriate for a particular embodiment. For example, in one embodiment, each micro-dispenser 24 may have its own mixer associated with it. A heating unit 28 or cooling unit 30 may be associated with the mixer 18 in order to alter temperature of the mixture so as to control viscosity of the mixture in a manner that will support printing. Any number of different types of heating and/or cooling may be used.

The micro-dispensers 24 may 3D print or dispense the materials in various dosage forms 26. The 3D printer may print or dispense the materials in multiple layers under computerized control to build-up the materials into dosage form. For example, the personalized medications may be dispensed into pre-existing capsules. Thus, for example, liquids or powders may be dispensed into the pre-existing capsules and then the capsules may be assembled or sealed. It is contemplated that a seal may be printed on the capsule to seal the capsule. The capsules may be placed in trays or on reels to assist in this process. Alternatively, the capsules themselves may be printed. Of course, capsules are not necessary as biopolymers may be printed in any number of different forms, including those which may be set by user preferences or according to prescription. For example, medication may be presented as strips, in sub-lingual form, or other types of oral dosages.

It is also to be understood that the personalized medicine described herein is not to be restricted to oral doses as other types of delivery systems are contemplated. For example, where medication is to be delivered as a patch, the patch or portions of the patch may be printed with the system in order to include a proper dose of the medication(s). Identifying information 32 may be included on the personalized medicine in the form of characters, symbols, patterns, or otherwise. Identifying information may also be conveyed based on size, shape, and coloring.

Figure 2:
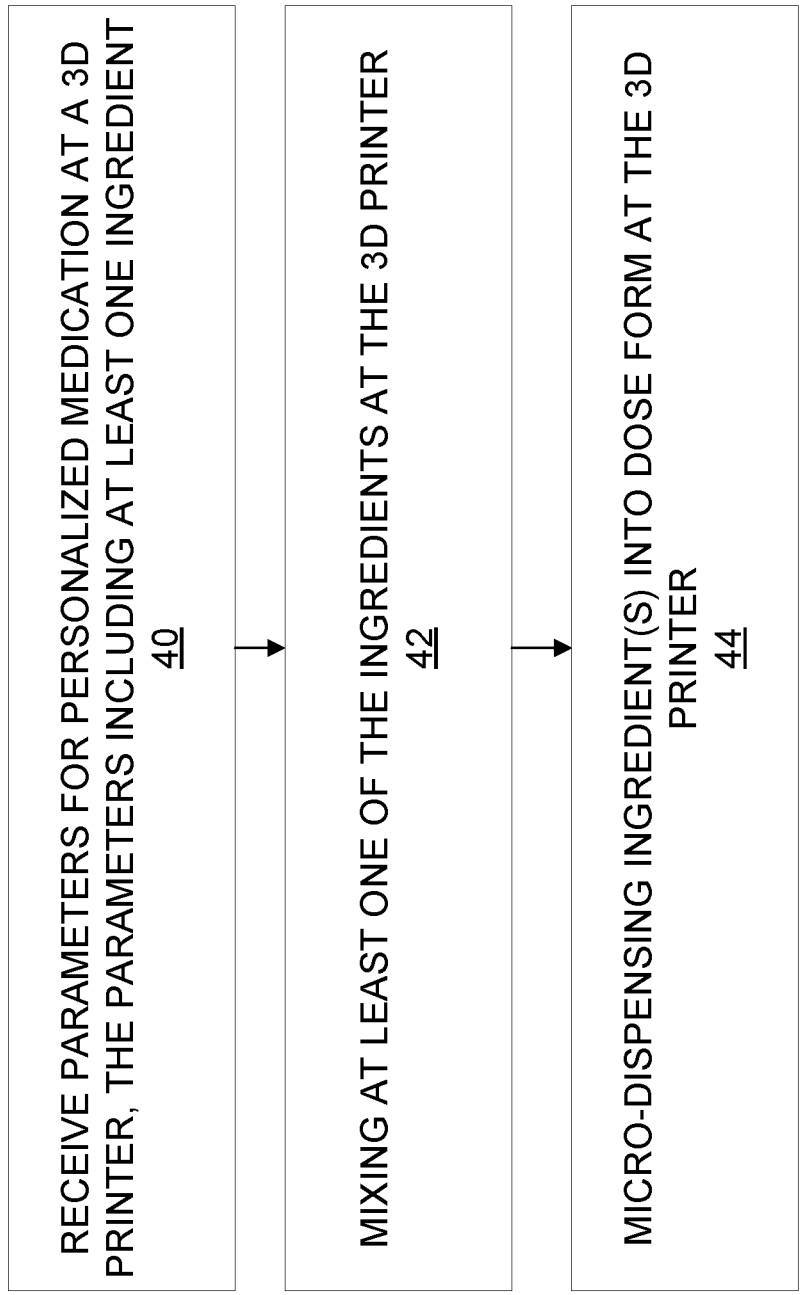
FIG. 2 is a flow chart according to one aspect.

FIG. 2 provides an overview of one methodology. In step 40, parameters for personalized medication or supplements are received at a 3D printer. The parameters may vary to include personal preferences, details of a prescription, or other parameters. The parameters define at least one ingredient. In step 42, one or more ingredients are mixed at a 3D printer. During mixing or in preparation for mixing the ingredients may be heated or cooled in order to obtain a desired viscosity. In step 44, the ingredients are micro-dispensed or 3D printed into dose form at the 3D printer.

The invention is not to be limited to the particular embodiments described herein. In particular, the invention contemplates numerous variations in the form of dose, the types of materials used, the specific type of micro-dispensing performed, the manner in which the process is controlled, the inputs to the system, and other variations. The foregoing description has been presented for purposes of illustration and description. It is not intended to be an exhaustive list or limit any of the invention to the precise forms disclosed. It is contemplated that other alternatives or exemplary aspects are considered included in the invention. The description is merely examples of embodiments, processes or methods of the invention. It is understood that any other modifications, substitutions, and/or additions can be made, which are within the intended spirit and scope of the invention.

What is claimed is:

1. A method for delivery of personalized medication or nutrition for an individual, the method comprising:
   receiving parameters for the personalized medication at a 3D printer, wherein the parameters comprise a plurality of ingredients, wherein the parameters vary concentrations of one or more of the plurality of ingredients in different layers to assist in promoting time release, wherein the 3D printer comprises a plurality of micro-dispensers with each of the plurality of micro-dispensers having a mixer;
   mixing at least one of the plurality of ingredients at the mixer of each of one or more of the micro-dispensers of the 3D printer to obtain the varying concentrations of the one or more of the plurality of ingredients specified by the parameters for each of the different layers; and
   micro-dispensing the plurality of the ingredients from the one or more micro-dispensers of the 3D printer in the different layers into dose form such that the different layers have varying concentrations of the one or more of the plurality of ingredients as specified by the parameters for each of the different layers.

2. The method of claim 1 wherein the micro-dispensing the one or more of the ingredients in the different layers into the dose form at the 3D printer comprises micro-dispensing the one or more of the ingredients into a pre-existing capsule.

3. The method of claim 1 wherein the one or more ingredients comprises at least one capsule ingredient and wherein the micro-dispensing the one or more of the ingredients in the different layers into the dose form at the 3D printer provides for forming a capsule and contents of the capsule.

4. The method of claim 1 wherein the dose form comprises a biopolymer.

5. The method of claim 1 further comprising applying heat during the mixing.

6. The method of claim 1 further comprising applying cooling during the mixing.

7. The method of claim 1 wherein at least one of the ingredients is a pharmaceutical agent.

8. The method of claim 1 wherein at least one of the ingredients is a flavoring agent.

9. The method of claim 1 wherein at least one of the ingredients is a coloring agent.

10. The method of claim 1 wherein the parameters are based at least in part on a prescription from a health care provider.

11. The method of claim 1 wherein the parameters are based at least in part on preferences of the individual.

12. The method of claim 1 wherein the parameters are for a set of doses with a varying amount of an active ingredient.

13. A system for delivery of personalized medication or nutrition for an individual, the system comprising:
   a 3D printing platform comprising a plurality of micro-dispensers;
   a plurality of mixers such that each of the plurality of micro-dispensers is associated with one of the plurality of mixers, each of the plurality of mixers for mixing at least one ingredient prior to micro-dispensing;
   a control system operatively connected to the 3D printing platform and the plurality of mixers;
   wherein the system is configured to:
      (a) receive parameters for the personalized medication at the control system, the parameters including a plurality of ingredients in powder or liquid form, wherein the parameters vary concentrations of the plurality of the ingredients in different layers to assist in promoting time release;
      (b) mix the plurality of the ingredients using the plurality of mixers associated with the plurality of micro-dispensers to obtain the concentrations of the plurality of the ingredients specified by the parameters; and
      (c) micro-dispense the different layers of the plurality of the ingredients into dose form using the plurality of micro-dispensers after mixing such that the different layers have varying concentrations of the one or more of the plurality of ingredients as specified by the parameters for each of the different layers.

14. The system of claim 13 wherein the system is configured to micro-dispense the plurality of the ingredients into a capsule.

15. The system of claim 13 wherein the system is configured to micro-dispense the plurality of the ingredients to form a capsule.

16. A method for delivery of personalized medication or nutrition for an individual according to a treatment program, the method comprising:
   receiving parameters for the personalized medication at a 3D printer for a plurality of doses, wherein the parameters for each of the plurality of the doses comprise a plurality of ingredients and volumetric information for the plurality of ingredients, wherein the parameters vary concentrations of the plurality of the ingredients in different layers for each of the plurality of the doses to assist in promoting time release, wherein the 3D printer comprises a plurality of micro-dispensers with each of the plurality of micro-dispensers having a mixer;
   mixing of the plurality of the ingredients using the mixer at each of one or more of the micro-dispensers of the 3D printer to obtain the varying concentrations of the plurality of ingredients specified by the parameters for each of the different layers; and
   micro-dispensing the different layers of the plurality of the ingredients into dose form from the one or more micro-dispensers of the 3D printer to form the plurality of doses for the treatment program;
   wherein the volumetric information for the plurality of ingredients is different for different ones of the doses within the treatment program.

17. The method of claim 16 wherein the each of the plurality of doses comprises identifying information.

18. The method of claim 17 wherein the identifying information is color coded.

19. The method of claim 17 wherein the identifying information comprises characters or symbols.

20. The method of claim 17 wherein the plurality of ingredients include a chief ingredient, an adjuvant, a corrective, and an excipient.

\* \* \* \* \*